US009492598B2

(12) United States Patent
Nour

(10) Patent No.: US 9,492,598 B2
(45) Date of Patent: Nov. 15, 2016

(54) EQUIPMENT THAT MAKES IT POSSIBLE TO APPLY A DETERMINED PULSATILE PRESSURE TO A MEDICAL DEVICE

(75) Inventor: Sayed Nour, Puteaux (FR)

(73) Assignee: CARDIO INNOVATIVE SYSTEMS-CIS, Paris (FR)

( * ) Notice: Subject to any disclaimer, the term of this patent is extended or adjusted under 35 U.S.C. 154(b) by 0 days.

(21) Appl. No.: 12/994,848

(22) PCT Filed: May 25, 2009

(86) PCT No.: PCT/FR2009/050965
§ 371 (c)(1),
(2), (4) Date: Feb. 8, 2011

(87) PCT Pub. No.: WO2009/153491
PCT Pub. Date: Dec. 23, 2009

(65) Prior Publication Data
US 2011/0166515 A1 Jul. 7, 2011

(30) Foreign Application Priority Data
May 27, 2008 (FR) ...................... 08 02871

(51) Int. Cl.
A61M 1/00 (2006.01)
A61M 1/10 (2006.01)

(52) U.S. Cl.
CPC ..................... A61M 1/106 (2013.01)

(58) Field of Classification Search
CPC .............. A61M 25/10; A61M 25/1018; A61M 25/0075; A61M 25/0074; A61M 35/00; A61M 1/1005; A61F 9/00
USPC ..................... 604/99.01, 99.02, 96.01, 97.01
See application file for complete search history.

(56) References Cited

U.S. PATENT DOCUMENTS

| 4,344,859 A * | 8/1982 | Burke, Jr. ...................... 366/241 |
| 2001/0016676 A1 | 8/2001 | Williams |
| 2007/0038174 A1* | 2/2007 | Hopkins ......................... 604/23 |

FOREIGN PATENT DOCUMENTS

| EP | 0972949 A1 | 1/2000 |
| EP | 1452195 A2 | 9/2004 |
| WO | 2007081612 A2 | 7/2007 |
| WO | WO2007/081612 * | 7/2009 .............. B60T 13/18 |

OTHER PUBLICATIONS

English translation of the International Search Report of the International Searching Authority dated Nov. 27, 2009.

* cited by examiner

Primary Examiner — Aarti B Berdichevsky
(74) Attorney, Agent, or Firm — Amster, Rothstein & Ebenstein LLP

(57) ABSTRACT

The invention relates to equipment for applying a determined pulsatile pressure to a medical device, comprising: a withdrawing means (2) designed to withdraw fluid from a source of fluid in continuous flow at high pressure; a conversion means (3) designed to convert said fluid into a fluid in a pulsatile flow at low pressure; at least one application means (105) for applying said fluid, as a low-pressure pulsatile flow, to said medical device; and a means (104) for removing said fluid.

5 Claims, 2 Drawing Sheets

EQUIPMENT THAT MAKES IT POSSIBLE TO APPLY A DETERMINED PULSATILE PRESSURE TO A MEDICAL DEVICE

CROSS REFERENCE TO RELATED APPLICATIONS

This application is a U.S. national stage entry under 35 U.S.C. §371 of PCT International Application No. PCT/FR2009/050965, filed on May 25, 2009, and claims priority to French Patent Application No. 0802871, filed on May 27, 2008, the contents of which are incorporated herein by reference in their entirety.

FIELD OF THE INVENTION

The present invention relates to an apparatus for applying a predetermined pulsating pressure on a medical device.

Hereinafter in the description, the term "medical device" should be understood to refer to a tube, catheter, suit or any other medical device.

BACKGROUND OF THE INVENTION

In conceptual terms, the cardiovascular system is a pressurised closed hydraulic circuit, lined internally by endothelial cells. The function of these endothelial cells is regulated by cardiac pulsation which induces pressure variations in the vessels and thus shearing of said cells, stimulating same. These tangential shear stress forces are essential for maintaining endothelial function comprising vascular tonicity via nitric oxide synthesis (NOS), blood clotting, inflammatory response, immunity, atherosclerosis, angiogenesis and apoptosis. The endothelial function is very important since it controls embryogenesis, morphogenesis, organogenesis and keeps the body healthy.

Any intervention on this circuit, such as, for example, a disease or a surgical operation, gives rise to endothelial dysfunction with potentially drastic consequences.

In the field of circulatory assistance, numerous pulsating apparatuses are currently used. These include, for example, External Enhanced Counter-Pulsation (EECP) apparatuses, Left Ventricular Assist Devices (LVAD), Intra-Aortic Balloon Pumps (IABP), etc.

However, to create this pulsating function, the current pulsating apparatuses available require consoles equipped with complex computer systems, electrocardiograms, cardiopulmonary monitors, alarms, etc. However, all these consoles are very costly, very bulky and required suitably trained nursing staff and engineers and technicians in order to function properly.

SUMMARY OF THE INVENTION

The invention thus proposes to simplify existing apparatuses by means of a novel apparatus for applying a predetermined pulsating pressure on a medical device.

Said apparatus for applying a predetermined pulsating pressure on a medical device comprises:
 drawing means suitable for drawing fluid from a high-pressure continuous flow fluid source;
 conversion means suitable for converting said fluid into a low-pressure pulsating flow fluid;
 at least one application means for applying said fluid, in a low-pressure pulsating flow on said medical device; and
 means for discharging said fluid.

Said apparatus has the advantage of being much simpler and smaller in size than existing consoles. It is thus less costly in respect of production and operation.

The apparatus according to the invention offers the advantage of creating the pulsatility applied on the medical device by means of a single high-pressure continuous flow fluid source. This fluid source may be that found in any medically equipped room, for example pressurised gas or liquid cylinders.

The apparatus according to the invention may be suitable for all types of medical devices, regardless of the size thereof, particularly existing medical devices.

For example, the medical device may be a balloon catheter and the application means is then connected to a fluid connection port connecting the apparatus according to the invention to the catheter balloon. The fluid from the apparatus according to the invention circulates in a pulsating manner to the balloon which makes pulsating inflation/deflation movements, creating a pulsating catheter.

In one embodiment of the invention, the apparatus according to the invention further comprises an enclosure, said enclosure being:
 suitable for being temporarily attached to the high-pressure continuous flow fluid source, to draw a finite fluid volume;
 attached to the drawing means to enable the drawing of the finite fluid volume contained therein; and
 attached to the discharge means to create a closed fluid circuit.

The presence of this enclosure makes it possible to draw a finite volume of high-pressure fluid. Once this volume of fluid has been drawn, the attachment between the enclosure, thus the apparatus according to the invention, and the fluid source may be removed. The apparatus according to the invention then becomes an autonomous apparatus.

The attachments of the enclosure to the drawing means and to the discharge means may be optionally permanent.

Since the discharge means is connected to said enclosure, the apparatus according to the invention has a closed fluid circuit. Therefore, there is no fluid loss. The apparatus according to the invention may operate in a portable manner provided that the drawn volume is sufficient to supply the entire enclosure-conversion means-application means-discharge means circuit.

In one embodiment of the invention, the apparatus according to the invention further comprises a hollow body having two ends and, from the periphery to the centre of the hollow body, an outer wall, a hollow chamber and a flexible membrane defining a through passage joining both ends, suitable for inserting a medical device, said application means passing through said outer wall, leading to the hollow chamber and being suitable for applying a pulsating pressure on the flexible membrane, and the discharge means coming from the hollow chamber and passing through said outer wall.

During operation, the medical device is inserted into the through passage and the fluid, in a low-pressure pulsating flow, is applied, via the hollow chamber, on the flexible membrane. The flexible membrane undergoes a compression/decompression movement transmitted to the medical device. The medical device is thus a pulsating device.

In a further embodiment, the apparatus according to the invention further comprises an enclosure as defined above and a hollow body as defined above.

In one embodiment of the invention, said conversion means is a piston-spring and compartment system.

This piston-spring assembly associated with a compartment is a relatively simple system for converting a continuous high-pressure fluid source into rhythmic low-pressure fluid pulsations (see hereinafter).

In one embodiment, said conversion means is controlled electromechanically.

The presence of an electromechanical control enables an operator to control the operation of the piston-springs and thus select the desired pulsation frequency and pressure.

In one embodiment, the apparatus according to the invention further comprises monitoring and alarm means. These monitoring and alarm means make it possible, for example, to detect any fluid leakage, measure the oxygen content in the patient's blood or the patient's heart rate and trigger an alarm in the event of danger and/or stop the pulsations from the apparatus.

In one particular embodiment, the electromechanical control and/or the monitoring and alarm means record an event log, by creation, for example, of a database suitable for subsequent operator queries.

The invention will be understood more clearly with reference to the appended figures, wherein:

DETAILED DESCRIPTION OF THE EXEMPLARY EMBODIMENTS

In the figures, the same reference numbers (unit and ten) refer to the corresponding structures between figures, the various alternative embodiments being distinguished by the hundred digits.

In the figures, the fluid circulation is represented by arrows.

Figure 1:
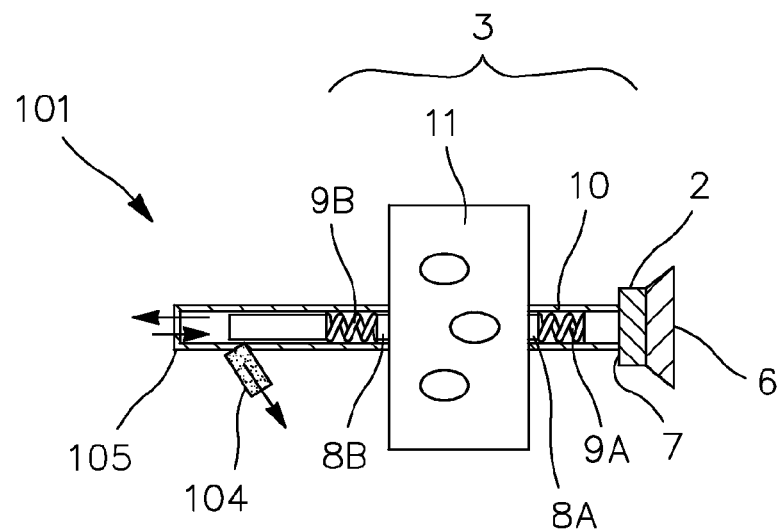
FIG. 1 is a schematic representation of a first embodiment of the invention for applying a pulsating pressure.

FIG. 1 represents the apparatus 101 according to the invention schematically in a longitudinal cross-section. This apparatus represented schematically with an overall long shape successively comprises from one end to the other: drawing means 2, conversion means 3, fluid discharge means 104 which, in this embodiment, discharges the fluid outside the apparatus according to the invention, and application means 105.

The drawing means 2 and the application means 105 will, generally but not necessarily, be extended by a high-pressure cord connecting the drawing means to the fluid source and by a low-pressure cord connecting the application means to the medical device.

The drawing means 2 may be in the form of a tube (having a roughly trapezium shape in FIG. 1) having two ends. The first end 6 of the drawing means 2 is suitable for tight attachment, via a high-pressure cord or directly, to a gas cylinder or to a gas supply present along the wall of the medically equipped room. The second end 7 of the drawing means 2 is attached to the conversion means 3.

The drawing means 2 and the conversion means 3 may be integral.

The conversion means 3, in the embodiment in FIG. 1, comprises an assembly of pistons 8A (high-pressure piston, located inside the compartment) and 8B (low-pressure piston, located outside the compartment) and springs 9A (high-pressure spring, which is a tensile spring) and 9B (low-pressure spring, which is a compressed spring) inserted into a tube 10 positioned on either side of a compartment 11 having two inlets. The pistons 8A and 8B, in operation, regularly open or close the inlets of the compartment 11. One end of the tube 10 is attached to the drawing means 2 and the other end consists, in this figure, of the application means 105. The conversion means 3 may be controlled electromechanically (control not represent in FIG. 1).

The discharge means 104 is situated on a portion of the tube 10 at the end consisting of the application means 105. This discharge means 104 may, for example, be a one-way valve.

During operation, if the apparatus 101 according to the invention is used with a balloon medical device, the application means 105, which in this embodiment is one end of the tube 10, is connected, via an optional low-pressure cord, to a fluid connection port (not represented), in turn connected to the medical device balloon. The drawing means 2 is attached, via an optional high-pressure cord, to a high-pressure continuous flow fluid source, for example a gas cylinder (not represented herein). This fluid source may have a pressure between 0.5 and 30 bar. Possible operation is as follows: high-pressure fluid, drawn from the continuous flow high-pressure fluid source enters the compartment 11 by pushing back the high-pressure piston 8A towards the inside of the compartment 11. Then, when the pressure inside the compartment 11 becomes equal to that of the high-pressure fluid, the high-pressure spring 9A, acting in the opposite direction to the continuous fluid flow, pulls piston 8A towards outside of the compartment 11 sealing the compartment 11. At the other side of the compartment 11, the low-pressure piston 8B is pushed back towards the outside of the compartment 11 by the pressure difference between the compartment 11 and the inside of the tube 10. Fluid comes out of the compartment 11 towards the tube 10 with a lower pressure than that of the compartment 11. Since the pressure in the compartment 11 drops, the low-pressure spring 9B pushes the low-pressure piston 8B back towards the compartment 11. Low-pressure fluid pulsation is thus created. An operating sequence has been described but it should be understood that this piston-spring-compartment system is in perpetual equilibrium and regularly creates low-pressure fluid pulsations directed to the application means 105.

In one preferred embodiment, the piston-spring-compartment system is coupled with an electromechanical control. In this way, according to the information provided by an operator to the electromechanical control, the pulsation frequency and the pressure of each pulsation may be selected by programming these data on said control. For example, the pulsation rate may be between 10 and 300 beats per minute. This rate may also be set to the patient's heart rate.

In the case of a balloon medical device, the fluid circulates in a pulsating manner from the application means 105, via the fluid connection means, to the medical device balloon to be discharged by the discharge means. The subsequent inflation/deflation of the balloon gives rise to a pulsating pressure on the medical device.

FIG. 1 represents a single application means 105. However, the apparatus according to the invention may have one or a plurality of application means. For example, when the medical device is a suit, it may be envisaged to have a first application means on the bottoms (with a first pulsation frequency and pressure) and a second application means at the waist (with a second pulsation frequency and pressure) and a third application means on the top (with a third pulsation frequency and pressure).

Figure 2:
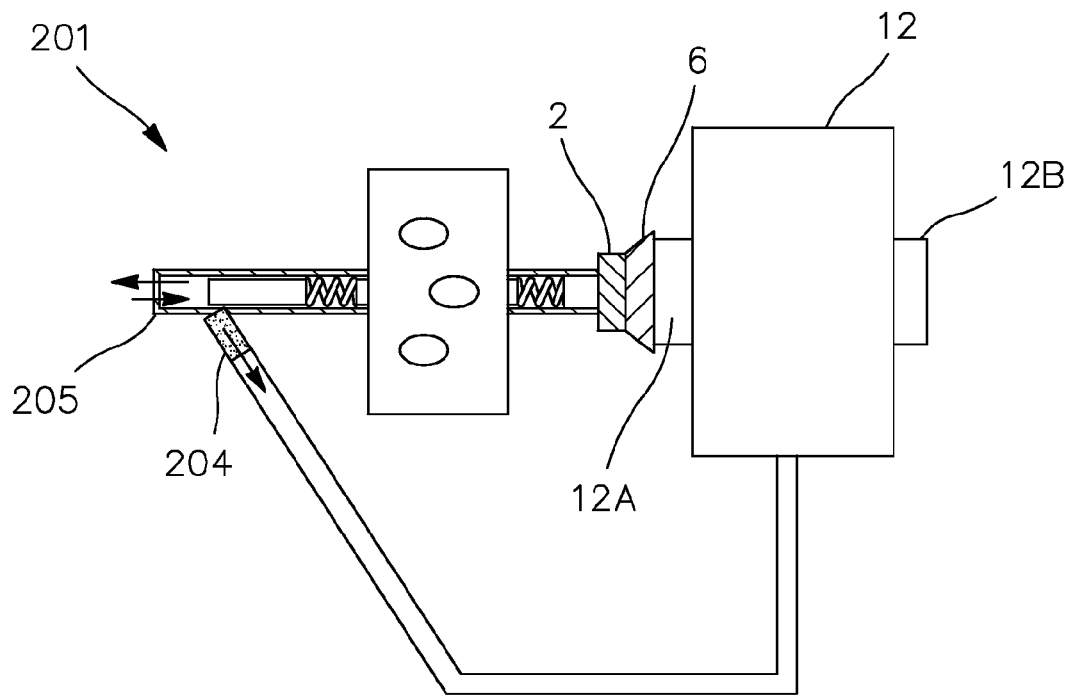
FIG. 2 is a schematic representation of a second embodiment of the invention, wherein the apparatus comprises an enclosure.

FIG. 2 represents a second embodiment of the invention differing from that in FIG. 1 in that the apparatus according to the invention 201 has an enclosure 12 and the discharge means 204 is connected to said enclosure 12.

The enclosure 12 is represented schematically in the form of a cube having two protuberances 12A and 12B, on two opposite sides, schematically representing accesses to the enclosure. At least the end 12B is an access suitable for being in the sealed or open position. The first protuberance 12A is attached to the end 6 of the drawing means 2 and the second protuberance 12B is suitable for attachment to the high-pressure continuous flow fluid source.

In this embodiment, the apparatus 201 is attached to the high-pressure continuous flow fluid source via the enclosure 12, at the end 12B. During operation, the end 12B is open and a finite fluid volume is drawn from the fluid source and enclosed in the enclosure 12 by sealing the end 12B. Said enclosure 12 is then detached from the fluid source. The apparatus 201 thus becomes autonomous.

To complete the autonomy of this apparatus 201, the discharge means 204 is connected to said enclosure 12, thus creating a closed fluid circuit (obviously, compression means should be envisaged to push the fluid from the low-pressure discharge means into the high-pressure enclosure 12).

During operation, if the apparatus 201 according to the invention is used with a balloon medical device, the piston-spring-compartment system dispenses fluid from the enclosure 12 in a low-pressure pulsating flow. If the fluid pulsation trajectory is described, it circulates via the application means 205 and the fluid connection port to inflate the medical device balloon. This fluid pulsation then returns to the discharge means 204 where it is routed, by compression, to the enclosure 12 while a further pulsation leaves the application means 205 for the medical device balloon.

Figure 3:
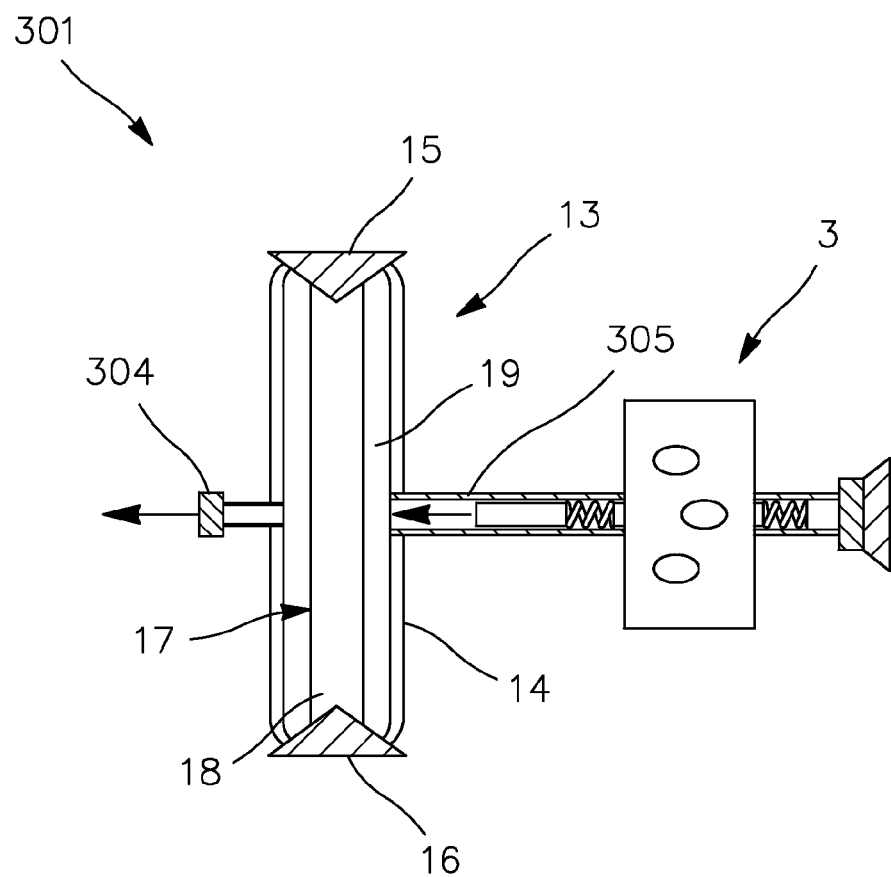
FIG. 3 is a schematic representation of a third embodiment of the invention, wherein the apparatus comprises a hollow body.

FIG. 3 represents a third embodiment of the invention differing from that in FIG. 1 in that the apparatus according to the invention 301 comprises a hollow body 13 attached to said application means 305. Said hollow body 13, which is preferably cylindrical with a circular cross-section, has an outer wall 14 and two ends 15 and 16. Said hollow body 13 contains a flexible membrane 17, which is also cylindrical, connecting to the two ends 15 and 16, and defining a through passage 18. Between the outer wall 14 and the flexible membrane 17, a hollow chamber 19 is created.

This embodiment creates a pulsating movement on a medical device devoid of a balloon, for example a tube, as explained hereinafter.

Due to the presence of said hollow body 13, the application means 305 is not connected to a fluid connection port but passes through the outer wall 14 and leads to the hollow chamber 19, the discharge means 304 from the hollow chamber 19 also passes through the outer wall 14. For example, the discharge means 304 may be in a diametrically opposed position to that of the application means 305.

When the apparatus 301 is not operating, the through passage 18 may be occupied by a bar and, at each end 15, 16, caps sealing the through passage 18 may be positioned. The presence of this bar and these caps removes any presence of vacuum in the apparatus for applying a pulsating pressure, when it is not in operation. No contaminants of any kind can thus contaminate the apparatus according to the invention.

During operation, the bar and the caps are removed from the apparatus 301. Instead of the bar, a medical device is inserted, and the fluid source (not represented) is opened.

The low-pressure pulsating flow fluid from the conversion means 3 circulates via the application means 305 to the hollow chamber 19. Two embodiments are then envisaged.

In the first, the pulsation of low-pressure fluid entering the hollow chamber 19 applies a pressure at a point of the flexible membrane 17, said pressure being passed onto the medical device. The fluid is then distributed in the hollow chamber 19 and the medical device is no longer subject to pressure. The discharge means 304 then only serves to drain the apparatus of any fluid. This operation is repeated for each pulsation, and a medical device subject to pulsating compression/decompression movements is thus obtained.

In the second embodiment, the low-pressure fluid pulsation represents a volume of fluid greater than the capacity of said hollow chamber 19, which compresses the flexible membrane 17 against the medical device. The discharge means 304 is then opened and the hollow chamber 19 is drained of this excess fluid, the membrane 17 no longer being compressed against the walls of the medical device. This operation is repeated for each pulsation, and a medical device subject to pulsating compression/decompression movements is again obtained.

The present invention is not limited to the embodiments described and represented. For example, in the conversion means, a stop valve system could be envisaged instead of the piston-spring system. Similarly, one embodiment of the apparatus according to the invention could associate an enclosure 12 and hollow body 13.

The invention claimed is:

1. Apparatus that applies a predetermined pulsating pressure on a medical device, the medical device being a tube, catheter or suit, comprising:

drawing means for drawing a continuous flow high-pressure fluid from a fluid source;

conversion means for converting the continuous flow high-pressure fluid into a low-pressure pulsating flow fluid, both the high-pressure fluid and the low-pressure pulsating flow fluid originating from the fluid source, the conversion means comprising:
 a compartment comprising a first inlet at one side of the compartment and a second inlet at another side of the compartment;
 a tube comprising a first portion in direct fluid communication with the drawing means and the first inlet and a second portion in direct fluid communication with the second inlet and at least one application means;
 a high pressure piston positioned within the first portion of the tube;
 a high pressure spring positioned within the first portion of the tube;
 a low pressure piston positioned within the second portion of the tube; and
 a low pressure spring positioned within the second portion of the tube;

the at least one application means is configured for attachment to the tube, catheter or suit and applies the low-pressure pulsating flow fluid on said medical device at a pulsation rate between 10 and 300 beats per minute so that with each pulse:
 high pressure fluid pushes the high pressure piston to open the first inlet;
 high pressure spring pulls high pressure piston to close the first inlet upon equalization of pressure between interior of compartment and pressure of the low-pressure pulsating flow fluid;

low pressure piston is pushed back to open the second inlet to thereby deliver the low-pressure pulsating flow fluid to a medical device; and low pressure spring pushes back on low pressure piston to close the second inlet upon drop of fluid pressure within the container resulting from opening of second inlet; and means for discharging the low-pressure pulsating flow fluid.

2. Apparatus for applying a predetermined pulsating pressure on a medical device according to claim 1, further comprising an enclosure, said enclosure being:

suitable for being temporarily attached to the high-pressure continuous flow fluid source, to draw a finite fluid volume;

attached to the drawing means to enable the drawing of the finite fluid volume contained therein; and attached to the discharge means to create a closed fluid circuit.

3. Apparatus for applying a predetermined pressure on a medical device according to claim 1, further comprising a hollow body having two ends and, from the periphery to the centre of the hollow body, an outer wall, a hollow chamber and a flexible membrane defining a through passage joining both ends, suitable for inserting the medical device, said application means passing through said outer wall, leading to the hollow chamber and being suitable for applying a pulsating pressure on the flexible membrane and the discharge means coming from the hollow chamber and also passing through said outer wall.

4. Apparatus for applying a predetermined pressure on a medical device according to claim 1, wherein the conversion means is controlled electromechanically.

5. Apparatus for applying a predetermined pressure on a medical device according to claim 1, further comprising monitoring and alarm means.

* * * * *